US009089639B2

(12) United States Patent
Breuel et al.

(10) Patent No.: US 9,089,639 B2
(45) Date of Patent: Jul. 28, 2015

(54) METHOD AND DEVICE FOR CONTROLLING AN EXTRACORPOREAL BLOOD TREATMENT APPARATUS

(75) Inventors: Lars Breuel, Erfurt (DE); Thomas Lindner, Forcheim/Ofr. (DE); Josef Beden, Mainz-Kastel (DE); Martin Herklotz, Heusenstamm (DE); Georg Verch, Wiesbaden (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 610 days.

(21) Appl. No.: 13/362,377

(22) Filed: Jan. 31, 2012

(65) Prior Publication Data

US 2012/0193290 A1    Aug. 2, 2012

Related U.S. Application Data

(60) Provisional application No. 61/438,275, filed on Feb. 1, 2011.

(30) Foreign Application Priority Data

Feb. 1, 2011  (DE) .......................... 10 2011 010 067

(51) Int. Cl.

| B01D 61/32 | (2006.01) |
|---|---|
| A61M 1/16 | (2006.01) |
| A61M 1/34 | (2006.01) |

(52) U.S. Cl.
CPC ............... *A61M 1/16* (2013.01); *A61M 1/1643* (2014.02); *A61M 1/342* (2013.01); *A61M 1/3451* (2014.02); *A61M 2205/3393* (2013.01)

(58) Field of Classification Search
CPC . A61M 1/34; A61M 2205/3334; A61M 1/16; A61M 1/3621; A61M 1/1643; A61M 1/342; A61M 1/3451; A61M 2205/3393
USPC ............. 210/645, 646, 650, 739, 744, 85, 86, 210/87, 97, 102, 103, 104, 109, 134, 143, 210/252, 257.2, 258, 321.65; 604/4.01, 604/5.01, 5.04, 6.09, 6.11, 28, 30; 137/565.29

See application file for complete search history.

(56) References Cited

U.S. PATENT DOCUMENTS

| 4,684,460 A | 8/1987 | Issautier | |
|---|---|---|---|
| 5,695,092 A * | 12/1997 | Schrandt | .......................... 222/1 |

(Continued)

FOREIGN PATENT DOCUMENTS

| EP | 1 543 853 A1 | 6/2005 |
|---|---|---|
| EP | 2 019 296 A1 | 1/2009 |
| WO | 98/50091 A1 | 11/1998 |

OTHER PUBLICATIONS

International Preliminary Report on Patentability (IPRP) dated Aug. 6, 2013 in PCT/EP2012/000292.

*Primary Examiner* — John Kim
(74) *Attorney, Agent, or Firm* — Kenyon & Kenyon LLP

(57) ABSTRACT

A method and device for controlling an extracorporeal blood treatment apparatus, which can be operated as a hemodialysis apparatus, hemofiltration apparatus or hemodiafiltration apparatus, are disclosed. The method and device make provision, apart from balancing the fluids as a function of the weights of the containers, for the measurement of the weight reduction or increase of at least one of the containers in the time interval in which the pump assigned to the respective container performs a preset number of revolutions or pump strokes. The change in the weight of the container for a half or one pump revolution can be determined. The delivery rate of the respective pump is ascertained from the measured weight reduction or increase in the specific time interval, thereby permitting the precise determination of the actual delivery rate of one or more pumps. The actual delivery rates of all the pumps are preferably monitored.

19 Claims, 2 Drawing Sheets

(56) References Cited

U.S. PATENT DOCUMENTS

| | | |
|---|---|---|
| 5,776,345 A | 7/1998 | Truitt et al. |
| 8,140,274 B2 * | 3/2012 | Gagel et al. ............... 702/45 |
| 8,246,566 B2 * | 8/2012 | Lannoy ................. 604/5.04 |
| 2004/0267183 A1 | 12/2004 | Chevallet |
| 2009/0276099 A1 | 11/2009 | Fujii et al. |
| 2010/0135824 A1 * | 6/2010 | Ickinger et al. ............ 417/43 |

* cited by examiner

METHOD AND DEVICE FOR CONTROLLING AN EXTRACORPOREAL BLOOD TREATMENT APPARATUS

CROSS REFERENCE TO RELATED APPLICATIONS

This application claims priority to U.S. Provisional Application Ser. No. 61/438,275 filed Feb. 1, 2011 and German Patent Application No. 10 2011 010 067.9 filed Feb. 1, 2011, both of which are herein incorporated by reference in their entireties.

FIELD OF INVENTION

The present invention relates to a method and a device for controlling an extracorporeal blood treatment apparatus, which can be operated in particular as a hemodialysis apparatus, a hemofiltration apparatus or a hemodiafiltration apparatus. Moreover, the present invention relates to an extracorporeal blood treatment apparatus with such a control device.

BACKGROUND OF THE INVENTION

In a hemodialysis treatment, the blood to be treated flows through the first chamber of a dialyzer, which is divided by a semipermeable membrane into a first chamber and a second chamber, whilst dialyzing fluid flows through the second chamber of the dialyzer. The hemodialysis treatment requires the balancing of fresh dialyzing fluid against used dialyzing fluid, in order to control the quantity of fluid fed to and removed from the patient. In hemodialysis, great demands are made on the balancing of the fluids.

In the case of acute dialysis for use in intensive care units, extracorporeal blood treatment apparatuses are used in which the fluids required for the blood treatment are made available in containers, in particular in bags. In the case of the known hemodiafiltration apparatuses for acute dialysis, dialyzing fluid and substituate are made available in bags, whilst filtrate is collected in a bag. To convey the fluids, use is made of peristaltic pumps, on the delivery accuracy of which great demands are made in order that the flow rate of dialyzing fluid, substituate and filtrate can be precisely adjusted.

The balancing of the fluids takes place in the case of the blood treatment apparatuses intended to be used in intensive care units by the fact that the weight of the bags filled with the fluids is monitored. The known blood treatment apparatuses comprise balances for this purpose. The flow rates for dialyzing fluid (dialysate), substituate and filtrate are preselected for the blood treatment, said flow rates being adjusted with the peristaltic pumps. However, since the actual delivery rates of peristaltic pumps, in particular roller pumps, diverge in practice from the setpoint delivery rates adopted in the drive circuit, incorrect balancing may occur. The exact balancing is achieved by the fact that the delivery rate of one or more pumps is changed in such a way that the difference between the weight reduction per unit of time of the dialysate bag and the substituate bag and the weight increase per unit of time of the filtrate bag corresponds to a preset value. If no fluid is to be removed from the patient, the pumps are regulated in such a way that the sum of the weight reduction of dialysate and substituate exactly corresponds to the weight increase of filtrate. Otherwise, a specific quantity of fluid is fed to or removed from the patient (ultrafiltration).

In the balancing, account must be taken if further fluids, for example heparin or citrate and calcium, are administered to the patient for the purpose of anticoagulation. The administration of further fluids can be taken into account by a manual adjustment carried out by the operator or automatically with the filtrate flow. For reasons of simplification, however, this will not be discussed further in the following description.

Only the measurement of the sum of the weight of the dialysate bag and substituate bag on the one hand and the weight of the filtrate bag on the other hand is in principle required for the balancing. Consequently, blood treatment apparatuses are known which comprise only two balances. Blood treatment apparatuses with three balances are however also known, wherein the dialysate bag and substituate bag are weighed with separate balances, so that the weight of each individual bag can be determined.

The control unit of the known blood treatment apparatuses provides a specific control range for the flow rates of the pumps, which in practice can amount to, for example, ±20% of the adjusted setpoint flow. If incorrect balancing is present, the incorrect balancing can be compensated for by changing the flow rate of one or more pumps within the control range. For example, in the case where the actual delivery rate of the dialysate pump is less than the setpoint delivery rate adopted in the drive circuit, the delivery rate of the dialysate pump can be increased accordingly. In order to compensate for the incorrect balancing, however, the required increase in the delivery rate of the dialysate pump must lie within the control range, i.e. for example within the control range of ±20% of the setpoint flow rate, in order to compensate for the incorrect balancing. The control cycle amounts to, for example, 1 second.

The known balances for weighing the bags are precision balances, which have to be checked on a regular basis. Known blood treatment apparatuses therefore provide cyclical tests of the balances which are carried out automatically. The cyclical balance tests are intended to avoid not only incorrect balancing due to errors with the balances, but also incorrect balancing caused by leakages in the hose system, which are revealed in the balance tests by an unpermitted drift of the measured values.

For a cyclical test of the balances, the pumps must be stopped in order to allow the balances to be checked. An attempt is therefore made to keep the number of cyclical tests as low as possible. The interval between successive balance tests must be selected in such a way that the incorrect balancing remaining undetected in the meantime cannot be greater than a specific value, for example 500 ml. In order to remain undetected in the meantime, a balance error or a leakage in the hose system must be so small that the balance error or the leakage can be compensated for by the permitted control range of, for example, ±20% of the adjusted setpoint flow, so that a balancing deviation cannot occur. The time interval between the balance tests is therefore dependent on the flow rate and the permitted control range. The time intervals between the cyclical balance tests are therefore also fixed in order to avoid the limiting value for incorrect balancing between two cyclical balance tests being exceeded. The smaller the permitted control range, therefore, the greater the interval between the cyclical balance tests can be selected.

SUMMARY OF THE INVENTION

One problem underlying the present invention is to provide a method for controlling an extracorporeal blood treatment apparatus, which permits exact balancing of the fluids and an extension of the intervals for the tests on the balances, especially when only the sum of the weight of the two fluids is measured for the balancing of the fluids. Furthermore, a problem underlying the present invention is to make available a device for controlling an extracorporeal blood treatment apparatus, which enables precise balancing with extended intervals for the balance tests. Another problem underlying the present invention is also to make available an extracorporeal blood treatment apparatus with such a control device.

The basic principle of the method according to the present invention and the device according to the present invention lies in the combination of the balancing based on the weights of the fluid containers and the determination of the precise delivery rates of the pumps used to convey the fluids. A precise knowledge of the delivery rates permits a smaller control range of the pumps used for the balancing and thus enables balancing deviations due to errors with the balances, leakages in the system etc. to be detected earlier. A further advantage lies in the increase in the treatment efficiency due to the extension of the intervals for the tests on the balances. The advantages of a smaller control range become noticeable especially when only the sum of the weight of two containers filled with fluid is evaluated, for example only the sum of the weight of the dialysate bag and substitute bag is measured. In the case of an excessively large control range, there is then the risk of an excessively large proportion of the quantity of substitute not delivered, for example by the substitute pump being taken over by the dialysate pump, as a result of which exact balancing of the fluids can be guaranteed, but the efficiency of the blood treatment is however adversely affected overall. This is critical, especially since this error cannot be observed in the case of measurement of the sum of the weight of the dialysate bag and the substitute bag.

The method according to the present invention and the device according to the present invention are intended for an extracorporeal blood treatment apparatus, with which a number of kinds of treatment, for example hemodialysis, hemofiltration or hemodiafiltration, can be carried out. The extracorporeal blood treatment apparatus comprises an exchange unit, such as a membrane mass exchange unit, which can be a dialyzer or a filter. Moreover, the blood treatment apparatus comprises three pumps for conveying fluids, i.e. dialysate, substitute and filtrate, from a container and respectively into a container. The dialysate and substitute are conveyed in each case from a container and the filtrate is conveyed into a container. The container can be a bag, in which fluid is made available or collected. Furthermore, the blood treatment apparatus comprises means for determining the sum of the weight of two containers and means for determining the weight of one container. The means for determining the weight of the containers are preferably balances. The means for determining the sum of the weight of two containers preferably comprise only one balance. Two balances can however also be used, the sum of the weight measured with each balance being calculated.

An alternative embodiment makes provision such that the first and third pump, i.e. the dialysate pump and substitute pump, can also deliver fluid from a common container. This alternative embodiment requires, however, that the dialysate and the substitute are the same fluid.

For the control of the pumps, the method according to the present invention and the device according to the present invention make provision, apart from balancing the fluids as a function of the weights of the containers, for the measurement of the weight reduction or weight increase of at least one of the containers in the time interval in which the pump assigned to the given container performs a preset number of revolutions or pump strokes. If it involves roller pumps, a specific number of revolutions is preset. Otherwise, a specific number of pump strokes is adopted. For example, the change in the weight of the container can be determined for a half or one pump revolution.

The delivery rate of the respective pump is ascertained from the measured weight reduction or weight increase in the specific time interval. The ascertainment of the weight reduction or weight increase per unit of time permits the precise determination of the actual delivery rate of one or more pumps. The actual delivery rates of the dialysate pump, the substitute pump and the filtrate pump are preferably monitored.

The control is basically governed by the setpoint delivery rate of the pumps, which may be the dialysate rate, filtrate rate or substitute rate, which is presumed to be known. This delivery rate adopted in the drive circuit, which should be adjusted with a preset number of revolutions per unit of time of the pump, is compared with the real delivery rate of the pump, i.e. the actual delivery rate.

The difference between the setpoint delivery rate and actual delivery rate is taken into account in the following drive circuit of the pumps. In practice, this can be carried out by the fact that, in the control of the pumps, an offset or correction factor is taken into account, which results from the ratio of the setpoint delivery rate to the actual delivery rate, referred to in the following as the base correction factor. If this base correction factor is dependent on the setpoint delivery rate, the base correction factor can be determined for an arbitrary number of different setpoint delivery rates and taken into account in the drive circuit of the pumps.

With the method according to the present invention and the device according to the present invention, therefore, the systematic deviations of the flow rates can already be taken into account in the drive circuit independently of the actual control, said deviations resulting from component-related deviations, for example due to tolerances of the geometrical dimensions of the pumps etc. and tolerances in the respective hose lines. A much smaller control range can be fixed for the pumps, because the systematic deviations no longer have to be compensated for by a regulation of the pumps. A smaller control range in turn means a lower risk of an excessively large proportion of the delivery volume of a pump being conveyed by another pump and enables an extension of the intervals between the tests on the balances. Overall, the blood treatment thus becomes more efficient. A brief departure from the limited tolerance range in the control of the pumps can be tolerated in order to allow balance malfunctions, for example, to be better compensated for.

A preferred embodiment of the present invention makes provision for the determination of the base correction factor of all the pumps. In principle, however, it is also possible to determine the base correction factor only for one pump or two pumps. The systematic error of the two other pumps or the other pump, however, cannot then be detected and the control range cannot therefore be reduced for the latter. The fixing of a particularly small control range for all the pumps involved in the balancing, therefore, is only possible when the base correction factor of all these pumps is ascertained.

In the preferred embodiment, in which the control of two pumps takes place by the determination of the change in weight on only one balance, the pump assigned to the same balance is stopped during the determination of the base correction factor of one pump. The change in the weight of the container can thus be assigned exclusively to the conveying pump.

In the case of hemodiafiltration, dialysate is fed to the second chamber of the exchange unit from a dialysate bag and filtrate is carried away from the second chamber of the exchange unit into a filtrate bag. Substituate is fed from a substituate bag to the extracorporeal blood circuit. Dialysate is conveyed by the first pump, filtrate by the second pump and substituate by the third pump. For the purpose of balancing the fluids, the pumps are controlled in such a way that the difference between the weight reduction per unit of time of the sum of the weights of the dialysate container and the substituate container and the weight increase per unit of time of the filtrate container corresponds to a preset value. If the preset value is 0, fluid is neither provided to nor withdrawn from the patient.

A preferred embodiment makes provision such that, in the determination of the base correction factor of a pump, the amount of the deviation of the setpoint delivery quantity of this pump from the actual delivery quantity with the preset number of revolutions or pump strokes is compared with a preset limiting value for a maximum deviation. If the amount of the deviation is greater than the preset limiting value, it is concluded that there is an error, an error signal being generated. If an error signal is generated, the measurement can be repeated. If the amount of the deviation is not calculated, it is possible to differentiate between a positive deviation upwards or a negative deviation downwards from a base value. For example, ±0.3 g per ½ revolution of the pump can be preset for a maximum deviation of the setpoint value from the actual value in practice. An upper and lower absolute limiting value can also be defined for the comparison of the deviation of the setpoint delivery quantity from the actual delivery quantity.

In principle, it is sufficient to carry out only a single measurement of the weight reduction or weight increase per unit of time, i.e. per revolutions or pump strokes. A greater accuracy can however be achieved by a plurality of measurements being carried out and a mean value being taken.

It is advantageous that the components required for the method according to the present invention and for the device according to the present invention are in any case generally present in the known blood treatment apparatuses. The measurement of the weight reduction or weight increase per unit of time with the balances in any case present for the balancing therefore does not require any additional expenditure on equipment. The control of the individual components can be taken over by the central control and computing unit, which is present in every blood treatment apparatus. The central control and computing unit of the blood treatment apparatus can also perform the necessary computational operations. The device according to the present invention, therefore, is preferably a component part of the extracorporeal blood treatment apparatus. It can however also be a separate assembly.

An example of embodiment of the present invention is explained in detail below by reference to the drawings, which show in a very simplified schematic representation the main components of two alternative embodiments of an extracorporeal blood treatment apparatus, wherein the balancing of the fluids takes place by means of balances. The parts corresponding to one another are provided with the same reference numbers in FIGS. 1 and 2.

The extracorporeal blood treatment apparatus is in particular a dialysis apparatus intended for acute dialysis in intensive care units, with which hemodialysis, hemofiltration or hemodiafiltration can be carried out.

DETAILED DESCRIPTION OF THE DRAWINGS

Figure 1:
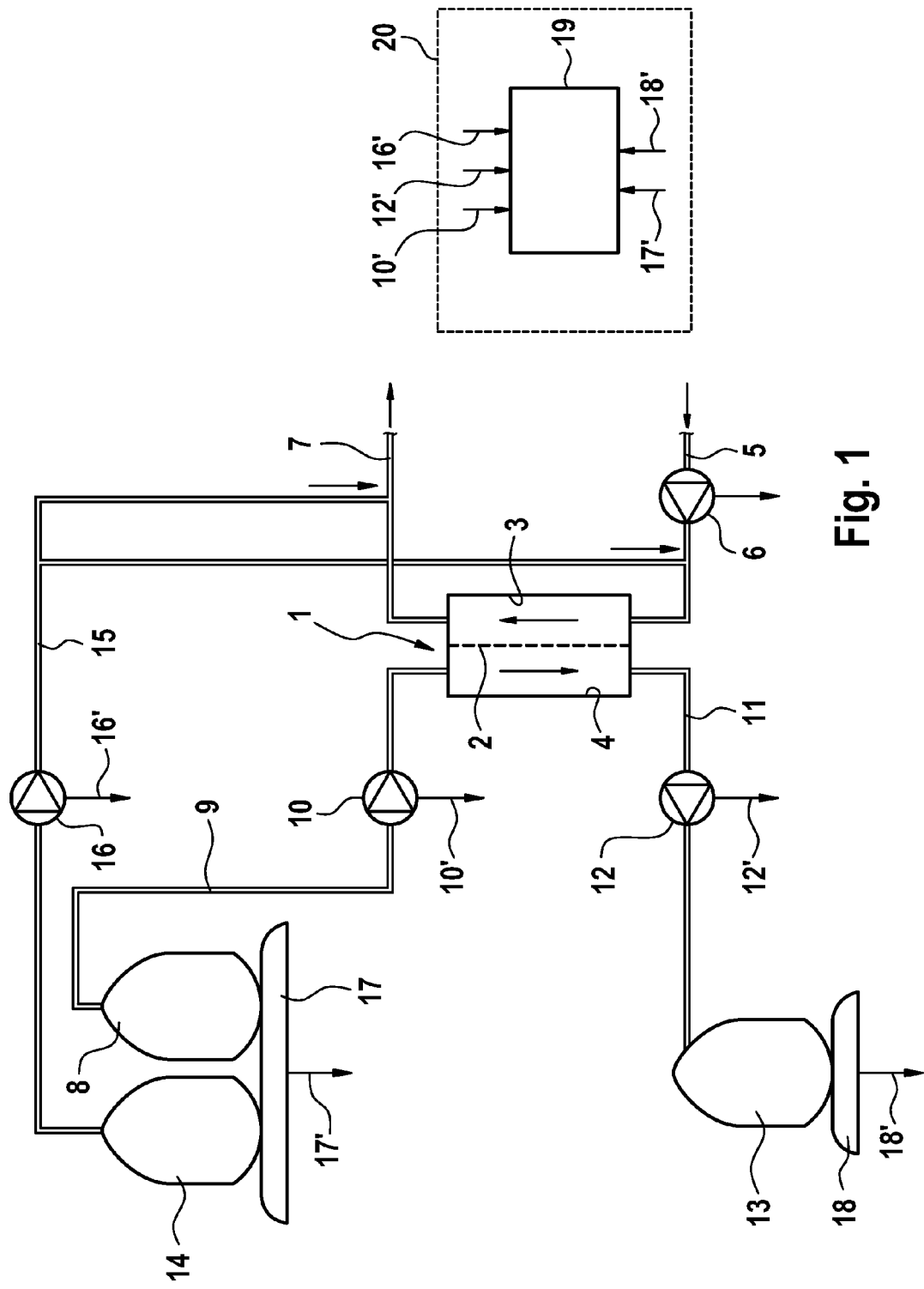
FIG. 1 shows a first embodiment of a blood treatment apparatus of the present invention.

The blood treatment apparatus comprises an exchange unit 1, which is divided by a semi-permeable membrane 2 into a first chamber 3 and a second chamber 4. The exchange unit is referred to below as dialyzer 1. Blood flows through first chamber 3 of dialyzer 1. The blood is conveyed via a blood supply line 5 from the patient by means of a blood pump 6 into first chamber 3 of dialyzer 1 and flows back to the patient via a blood discharge line 7 from first chamber 3 of dialyzer 1, as shown in FIG. 1.

For the blood treatment, dialyzing fluid (dialysate) is made available in a first container 8, which is preferably a bag. The dialysate is conveyed from dialysate bag 8 into second chamber 4 of dialyzer 1 via a dialysate line 9, into which a dialysate pump 10 is incorporated. From second chamber 4 of dialyzer 1, filtrate is conveyed through a filtrate line 11, into which a filtrate pump 12 is incorporated, into a filtrate container 13, in particular a filtrate bag. For the dialysis treatment, substituate is made available in a substituate container 14, in particular in a substituate bag. From substituate bag 14, the substituate is fed via a substituate line 15, into which a substituate pump 16 is incorporated, to the extracorporeal blood circuit either upstream of first chamber 3 of the dialyzer (pre-dilution) or downstream of first chamber 3 of dialyzer 1 (post-dilution).

Dialysate line 9, filtrate line 11 and substituate line 15, which are connected respectively to dialysate bag 8, filtrate bag 13 and substituate bag 14, are hose lines of a hose system intended for one-time use (disposable). Dialysate pump 10, filtrate pump 12 and substituate pump 16 are peristaltic pumps, in particular roller pumps, into which the hose lines are inserted. The roller pumps preferably comprise a stepping motor, the number of steps (revolutions) determining the delivery quantity of the pump. With each full or half revolution, each pump has a specific theoretical delivery quantity, on which the inserted hose line also has an influence. The setpoint delivery rate of the pump indicated by the manufacturer may however deviate from the actual delivery rate. Exact balancing of the fluids over the whole treatment period is therefore not guaranteed without compensation for this deviation. Another motor may also be used instead of a stepping motor. For example, a motor with brushes or a brushless motor with a standard clock generator can be used.

A balancing arrangement is provided for the exact balancing of the fluids, said balancing arrangement comprising a first balance 17 and a second balance 18. First balance 17 is used to weigh dialysate bag 8 and substituate bag 14, whilst filtrate bag 13 is weighed with second balance 18. Balances 17, 18 can be designed differently. For example, the bags can lie on the balances or hang from the balances. First balance 17 weighs the sum of the weight of the dialysate bag 8 and substituate bag 14, whilst the second balance 18 weighs only the weight of filtrate bag 13. Containers 8 and 14 may alternatively not be placed together on balance 17, but rather be placed on two separate balances.

In order to control dialysate pump 10, filtrate pump 12 and substituate pump 16, the control device according to the present invention comprises a control unit 19, which can be a component part of central control and computing unit 20 of the extracorporeal blood treatment apparatus. Control and computing unit 20 comprises a CPU for performing the calculations and the control.

Control unit 19 is connected via measurement lines 17', 18' to first balance 17 and second balance 18. Via control lines 10', 12' and 16', control unit 19 is connected to dialysate pump 10, filtrate pump 12 and substituate pump 16.

In order to perform the blood treatment, a specific delivery rate is first preset for dialysate pump 10, filtrate pump 12 and substituate pump 16 via an input unit (not shown). To adjust the delivery rates, control unit 19 presets a specific number of steps (revolutions) per unit of time for the stepping motors of the pumps. It is assumed that the desired delivery rate is also exactly set, although this is not the case in practice.

For example, a dialysate rate of 2000 ml/h and a substituate rate of 900 ml/h and a net ultrafiltration rate of 100 ml/h are adopted. A filtrate rate of 3000 ml/h (50 ml/min) results from this. Since the actual delivery rates of the pumps deviate from the setpoint delivery rates, the preset net ultrafiltration rate is not achieved in practice, which can lead to incorrect balancing.

For the balancing of the fluids, control unit 19 regulates the delivery rates of dialysate pump 10, filtrate pump 12 and substituate pump 16. The delivery rate of one or more pumps is thereby increased or reduced in a selective manner in order to compensate for the error. The adaptation of the delivery rates takes place within a preset control range. The delivery rate of one or more pumps should not be increased or reduced by an amount which is greater than a specific limiting value. This limiting value can be a percentage of the setpoint delivery rate, for example ±20%.

On the assumption that fluid is neither to be fed to nor withdrawn from the patient, i.e. the net ultrafiltration rate is 0, control unit 19 regulates the pumps in such a way that the sum of the weight reduction of dialysate bag 8 and substituate bag 14 in a specific unit of time, for example per minute or hour, corresponds to the weight increase of filtrate bag 13. In the case where fluid is to be withdrawn from the patient, the control unit 19 regulates the pumps in such a way that the amount of the difference between the weight reduction of the sum of the weight of dialysate bag 8 and substituate bag 14 and the weight increase in the weight of the filtrate bag 13 corresponds to the net ultrafiltration rate.

In the case of the above example of embodiment, a filtration rate of 3000 ml/h (50 ml/min) is adjusted to achieve the net ultrafiltration rate of 100 ml/h. With an assumed control range for the filtrate pump of ±20%, the filtrate rate can be increased or reduced by a maximum of ±10 ml/min. related to the setpoint value, in order to compensate for the error.

In order to avoid incorrect balancing, it is necessary to test balances 17, 18 at specific time intervals. The time intervals between the tests are governed according to the volume which can be delivered to or withdrawn from the patient undetected by the actual balancing (incorrect balance). If it is assumed that a pump is driven in the middle of the control range before a leakage for example, the incorrect balance rate in the assumed case could correspond to ±20%=±10 ml/min of the setpoint delivery rate. If, for example, the incorrect balance between two balance tests should not be greater than 500 ml, it is necessary in the present example of embodiment to carry out a balance test every 50 min. (500 ml/10 ml/min=50 min).

The mode of functioning of control unit 19 for controlling the extracorporeal blood treatment apparatus is described below using the example of hemodiafiltration. Dialysate pump 10 and substituate pump 16 deliver from a common balance 17. The present invention provides for a reduction in the control range. In the present example of embodiment, the control range should amount, for example, to only ±8% of the setpoint delivery rate.

Preferably before the actual blood treatment, central computing and control unit 20 of the blood treatment apparatus generates a control signal to initiate the determination of the base correction factor for pumps 10, 12, 16 involved in the balancing. The determination of the base correction factor can however also be initiated during the treatment or a pause in the treatment. The determination of the base correction factor preferably takes place during the treatment, e.g. 10 min. after the start of the treatment, when dialysate pump 10, filtrate pump 12 and substituate pump 16 are running.

After the control signal is received, control unit 19 stops substituate pump 16. The delivery rate of filtrate pump 12 is then adapted by the control unit 19 in such a way that the desired net ultrafiltration rate is re-established. For this purpose, the setpoint delivery rate of filtrate pump 12 is reduced by the flow of stopped pump 16.

The quantity of dialysate conveyed per revolution or per stroke of dialysate pump 10 is then determined, said quantity being denoted below as the stroke volume of the dialysate pump. For this purpose, the weight reduction of dialysate bag 8 is detected in the time interval in which the dialysate pump has performed a specific number of revolutions or strokes. The reduction in the volume of dialysate corresponding to the weight reduction in this time interval divided by the number of revolutions or strokes performed corresponds to the stroke volume of the dialysate pump to be measured. Control unit 19 preferably performs a large number of successive measurements for a half or a whole pump revolution, for example 20 measurements, and calculates the mean value from the ascertained stroke volumes.

Control unit 19 then puts substituate pump 16 back into operation and now stops dialysate pump 10. Control unit 19 now determines the stroke volume of substituate pump 16, in the same way as with dialysate pump 10. After determination of the stroke volume of substituate pump 16, dialysate pump 16 is put into operation again. When the stroke volume of substituate pump 16 is determined, the setpoint delivery rate of filtrate pump 12 is also reduced again by control unit 19 by the flow of pump 10 which is now stopped, so that the desired net ultrafiltration rate is established.

It is also possible for the aforementioned stopped pumps not to be stopped for the determination of the correction factor of another pump, but only to be reduced to a minimum in their flow. Accordingly, the flow of filtrate pump 12 can then be adjusted by the reduced flow.

The determination of the stroke volume of filtrate pump 13 takes place during the determination of the stroke volume of dialysate pump 10 and substituate pump 16. For this purpose, the weight increase of filtrate bag 13 is detected in each case in successive measurements within the time interval in which filtrate pump 12 performs a specific number of revolutions, a mean value of the ascertained stroke volumes being calculated.

After the determination of the stroke volumes of pumps 10, 12, 16, the stroke volume which was hitherto adopted in the control and which corresponds to the value stipulated by the manufacturer of the pumps, is related to the ascertained actual stroke volume of the pumps in order to determine a corresponding control factor, the base correction factor. The "zero line" for the pump drive is then shifted by the base correction factor thus determined. The pump drive thus takes place with a specific "offset". The share of the systematic flow deviations resulting from the tolerances of the pumps and of the expendable item (disposable) is thus taken into account, so that a smaller control range, for example ±8% of the setpoint flow rate, can be preset in order to extend the time intervals between the cyclical balance tests.

The base correction factor should not produce a greater offset than the maximum possible error in the setpoint delivery rate due to component-related deviations, for example of more than ±15%. If the ascertained base correction factor lies, for example, between ±15% and ±20%, it is limited by control unit 19 to ±15%. If the ascertained offset is more than ±20%, the determination of the stroke volume is not deemed to be successful and can be repeated by the user. Control unit 19 generates an error signal in this case.

During the determination of the base correction factor of the pumps, stroke volumes identified as disrupted are not used to determine the base correction factor. If an error is present, the measurement of the weight reduction or weight increase can be extended by the number of disrupted stroke volumes. Even if, in this way, more than a specific number of pump revolutions is required for the determination of the base correction factor, for example 25 pump revolutions, the calibration is deemed not to have been successfully passed and can be repeated by the user. Control unit 19 also generates an error signal in this case. In order to compensate for any long-duration deviations occurring in the stroke volumes, the base correction factor can still be corrected after completion of the calibration by means of a separate algorithm.

The determination of the stroke volumes does not have to be repeated during an ongoing treatment. Tests in the laboratory have shown that the stroke volume of the employed pumps, after a running-in time of approx. 5 minutes, scarcely displays any measurable drift over the following 70 hours. During the determination of the stroke volumes, the flow rates of the pumps can be limited to an upper value, which can lie for example at maximum 2000 ml/h, in order to increase the accuracy of the determination of the base correction factor.

It is intended to illustrate once again, on the basis of the following example, that the interval between the cyclical balance tests can be markedly increased when, after the determination of the stroke volumes of the pumps, the permitted control range for the filtrate pump is reduced.

For example:
Method: CVVHDF
Dialysate rate: 2000 ml/h
Substitute rate: 900 ml/h
Net ultrafiltration rate: 100 ml/h In order to adjust the desired net ultrafiltration rate, a filtrate rate of 3000 ml/h=50 ml/min. must be preset by the control unit. A filtrate control range of ±8%=±4 ml/min. is preset. Since the pump is driven precisely in the middle of the control range in the normal case, the incorrect balance rate resulting for example from a leakage can amount to only the one-sided control range of 8%=4 ml/min. If 500 ml is allowed as the maximum incorrect balance, a cyclical balance test results which should be performed every 125 min (500 ml/4 ml/min.=125). It emerges that the interval lying between the balance tests is greater than in the case of a control range of ±20%, with which the test interval is 50 min.

When the method according to the present invention and the device according to the present invention are used in hemodialysis, only the stroke volumes of the dialysate pump and filtrate pump need to be determined, since the substituate pump is not operated for hemodialysis.

When the method according to the present invention and the device according to the present invention are used in a hemofiltration (CVVH), only the stroke volumes of the substituate pump and filtrate pump need to be determined, because the dialysate pump is not operated for hemofiltration.

Figure 2:
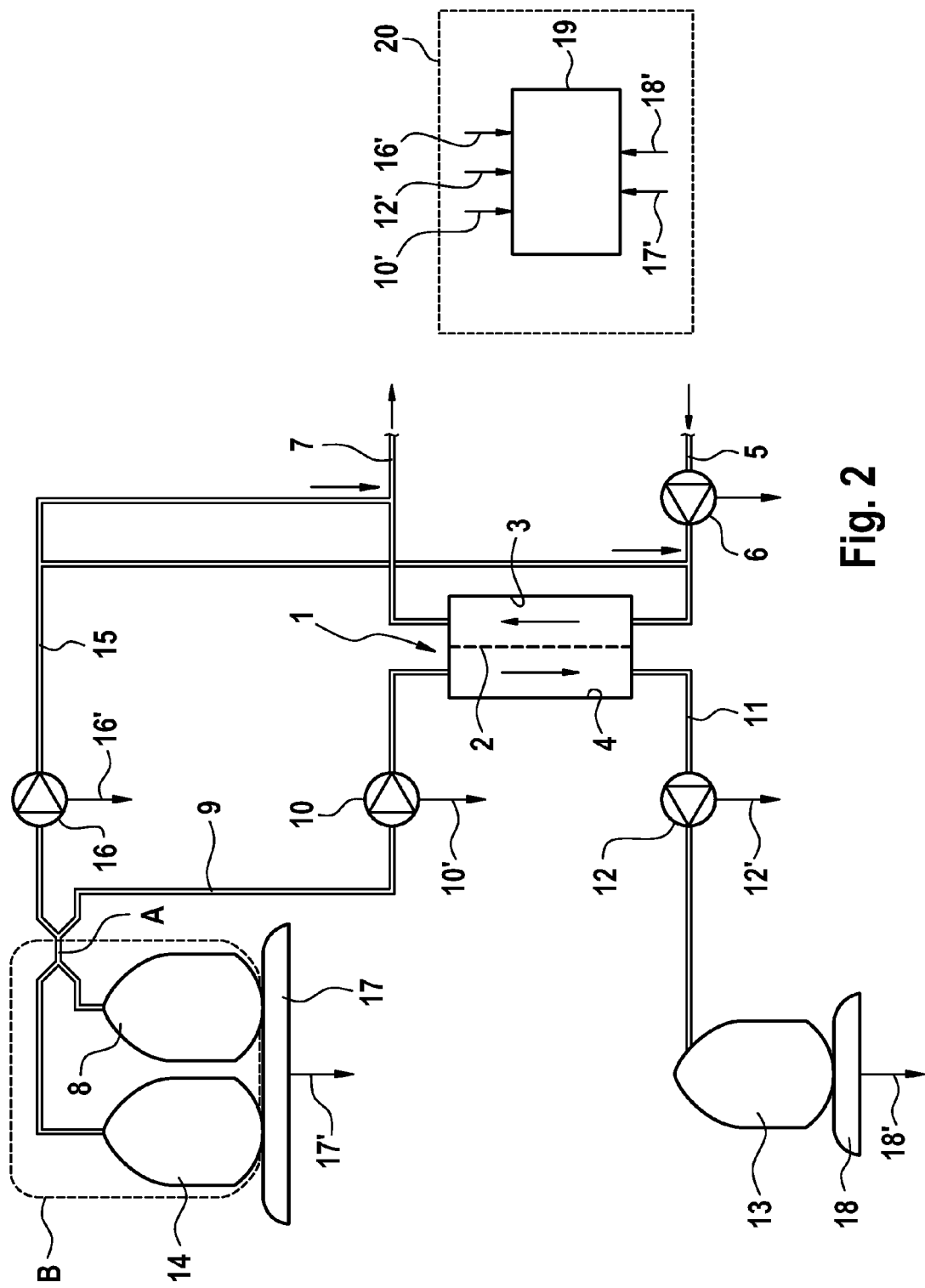
FIG. 2 shows a second embodiment of a blood treatment apparatus of the present invention.

FIG. 2 shows a second embodiment of the extracorporeal blood treatment apparatus, which differs from the first example of embodiment solely in that the two lines 9 and 15 from bags 8 and 14 comprise a common line segment A. For example, the two lines 9, 15 can be led together with a first Y-connection piece (not shown) to form common line segment A, which for example can have a length of 50 cm, and can be split again with a second Y-connection piece (also not shown). The composition of the dialysate and substituate in bags 8 and 14 respectively is in this case identical. The two bags 8, 14 act as a single bag. Instead of the two bags 8, 14, dialysate and substituate can therefore also be made available in a single bag, to which lines 9 and 15 are connected. This single container B, which replaces containers 8 and 14, is shown in dashed lines in FIG. 2 as a further alternative embodiment.

The second embodiment with the two bags and the common line segment has the handling advantage that the two bags 8 and 14 become empty simultaneously independently of the different flow rates of pumps 10 and 16. When the fluid is made available in only one bag, the problem of simultaneous emptying does not exist at all.

What is claimed is:

1. A method for controlling an extracorporeal blood treatment apparatus, said extracorporeal blood treatment apparatus comprising:

an exchange unit that is divided by a semi-permeable membrane into a first chamber and a second chamber, wherein the first chamber is part of an extracorporeal blood circuit and the second chamber is part of a fluid circuit;

a first pump for conveying a first fluid from a first container at a first delivery rate into the second chamber of the exchange unit;

a second pump for conveying a second fluid from the second chamber of the exchange unit at a second delivery rate into a second container;

a third pump for conveying a third fluid at a third delivery rate from a third container or from the first container into the extracorporeal blood circuit;

a first weighing device; and a second weighing device, said method comprising:

weighing the first container and the third container via the first weighing device or weighing the first container via the first weighing device and weighing the second container via the second weighing device;

regulating the first, second, and third pumps for balancing the first, second, and third fluids as a function of:

(I)(a) a sum of the weights of the first container and the third container, and (b) the weight of the second container; or (II)(a) the weight of the first container, and (b) the weight of the second container;

measuring a weight reduction or a weight increase of at least one of the first, second, or third containers in a time interval in which the first, second, or third pump assigned to the respective first, second, or third container performs a preset number of revolutions or pump strokes;

ascertaining a delivery quantity of the respective first, second, or third pump at the preset number of revolutions or pump strokes from the measured weight reduction or weight increase in the time interval;

comparing the setpoint delivery quantity of the respective first, second, or third pump at the preset number of revolutions or pump strokes adopted in a drive circuit of the respective first, second, or third pump with the measured delivery quantity of the respective first, second, or third pump at the preset number of revolutions or pump strokes; and basing the drive circuit of the first, second and third pumps on the deviation of the adopted setpoint delivery quantity of the respective first, second, or third pump at the preset number of revolutions or pump strokes from the measured delivery quantity of the first, second, or third pump at the preset number of revolutions or pump strokes.

2. The method according to claim 1, further comprising:
controlling the first, second, and third pumps for balancing the fluids in such a way that the difference between the weight reduction per unit of time of the sum of the weights of the first container and the third container, and the weight increase per unit of time of the second container, corresponds to a preset value.

3. The method according to claim 1, further comprising:
measuring the weight reduction of the first container in the time interval in which the first pump performs a preset number of revolutions or pump strokes, and ascertaining the delivery quantity of the first pump at the preset number of revolutions or pump strokes from the measured weight reduction;
measuring the weight increase of the second container in the time interval in which the second pump performs a preset number of revolutions or pump strokes, and ascertaining the delivery quantity of the second pump at the preset number of revolutions or pump strokes from the measured weight increase
measuring the weight reduction of the third container in the time interval in which the third pump performs a preset number of revolutions or pump strokes, and ascertaining the delivery quantity of the third pump at the preset number of revolutions or pump strokes from the measured weight reduction; and
comparing the delivery quantities of the first, second, and third pumps at the preset number of revolutions or pump strokes adopted in the drive circuit of the first, second, and third pumps with the measured delivery quantities of the first, second, and third pumps at the preset number of revolutions or pump strokes, and basing the drive circuit of the first, second, and third pumps on the deviation of the adopted delivery quantities of the first, second, and third pumps at the preset number of revolutions or pump strokes from the measured delivery quantities of the first, second, and third pumps at the preset number of revolutions or pump strokes.

4. The method according to claim 1, wherein the first weighing device comprises a first balance for the simultaneous weighing of the first container and the third container, and the second weighing device comprises a second balance for weighing the second container.

5. The method according to claim 4, further comprising:
determining the weight reduction of the first container by stopping the third pump or reducing the flow rate of the third pump in the time interval in which the first pump performs the preset number of revolutions or pump strokes.

6. The method according to claim 5, further comprising:
determining the weight reduction of the third container by stopping the first pump or reducing the flow rate of the first pump in the time interval in which the third pump performs a preset number of revolutions or pump strokes.

7. The method according to claim 6, further comprising:
increasing or decreasing the preset setpoint delivery rate of at least one of the first, second, or third pumps within a preset control range by a specific amount which is less than a preset limiting value, so that the difference between the weight reduction per unit of time of the sum of the weights of the first container and the third container, and the weight increase per unit of time of the second container, corresponds to a preset value.

8. The method according to claim 7, wherein the preset limiting value is a preset percentage of the preset setpoint delivery rate of the respective first, second, or third pump.

9. The method according to claim 8, further comprising:
comparing the deviation of the adopted delivery quantity of the respective first, second, or third pump at the preset number of revolutions or pump strokes from the measured delivery quantity of the first, second, or third pump at the preset number of revolutions or pump strokes with a preset limiting value; and
generating an error signal when the deviation is greater than the limiting value.

10. A device for controlling an extracorporeal blood treatment apparatus, wherein the extracorporeal blood treatment apparatus comprises:
an exchange unit that is divided by a semi-permeable membrane into a first chamber and a second chamber, wherein the first chamber is part of an extracorporeal blood circuit and the second chamber is part of a fluid circuit;
a first pump for conveying a first fluid from a first container at a first delivery rate into the second chamber of the exchange unit;
a second pump for conveying a second fluid from the second chamber of the exchange unit at a second delivery rate into a second container;
a third pump for conveying a third fluid at a third delivery rate from a third container or from the first container into the extracorporeal blood circuit;
a first weighing device configured to weigh the first container and the third container or configured to weigh the first container; and
a second weighing device configured to weigh the second container;
wherein the device for controlling the extracorporeal blood treatment apparatus comprises:
a control unit for controlling the delivery rates of the pumps, wherein said control unit is configured to balance the fluids as a function of:
(I)(a) the sum of the weights of the first container and the third container, and (b) the weight of the second container; or
(II)(a) the weight of the first container, and (b) the weight of the second container;
wherein a weight reduction or a weight increase of at least one of the first, second, or third containers is measured in the time interval in which the first, second or third pump assigned to the respective first, second, or third container performs a preset number of revolutions or pump strokes;
the delivery quantity of the respective first, second, or third pump at the preset number of revolutions or pump strokes is ascertained from the measured weight reduction or weight increase in the time interval;
the setpoint delivery quantity of the first, second, and third pumps at the preset number of revolutions or pump strokes adopted in the drive circuit of the respective first, second, or third pump is compared with the measured delivery quantity of the first second, or third pump at the preset number of revolutions or pump strokes; and
the drive circuit of the first, second, and third pumps is based on the deviation of the adopted setpoint delivery quantity of the respective first, second, or third pump at the preset number of revolutions or pump strokes from the measured delivery quantity of the first, second, or third pump at the preset number of revolutions or pump strokes.

11. The device according to claim 10, wherein the control unit is configured such that, in order to balance the fluids, the delivery rates of the first, second, or third pumps are set in such a way that the difference between the weight reduction per unit of time of the sum of the weights of the first container and the third container and the weight increase per unit of time of the second container corresponds to a preset value.

12. The device according to claim 10, wherein the control unit is configured such that:
the weight reduction of the first container is measured in the time interval in which the first pump performs a preset number of revolutions or pump strokes, and the delivery quantity of the first pump at the preset number of revolutions or pump strokes is ascertained from the measured weight reduction;
the weight increase of the second container is measured in the time interval in which the second pump performs a preset number of revolutions or pump strokes, and the delivery quantity of the second pump at the preset number of revolutions or pump strokes is ascertained from the measured weight increase;
the weight reduction of the third container is measured in the time interval in which the third pump performs a preset number of revolutions or pump strokes, and the delivery quantity of the third pump at the preset number of revolutions or pump strokes is ascertained from the measured weight reduction; and
the delivery quantities of the first, second, and third pumps at the preset number of revolutions or pump strokes adopted in the drive circuit of the first, second, and third pumps are compared with the measured delivery quantities of the first, second, and third pumps at the preset number of revolutions or pump strokes, and the drive circuit of the first, second, and third pumps is based on the deviation of the adopted delivery quantities of the first, second, and third pumps at the preset number of revolutions or pump strokes from the measured delivery quantities of the first, second, and third pumps at the preset number of revolutions or pump strokes.

13. The device according to claim 12, wherein the first weighing device comprises a first balance for the simultaneous weighing of the first container and third container, and the second weighing device comprises a second balance for weighing the second container.

14. The device according to claim 13, wherein the control unit is configured such that for the determination of the weight reduction of the first container, the third pump is stopped or the flow rate of the third pump is reduced in the time interval in which the first pump performs a preset number of revolutions or pump strokes.

15. The device according to claim 14, wherein the control unit is configured such that for the determination of the weight reduction of the third container, the first pump is stopped or the flow rate of the first pump is reduced in the time interval in which the third pump performs a preset number of revolutions or pump strokes.

16. The device according to claim 10, wherein the control unit is configured such that the preset setpoint delivery rate of at least one of the first, second, or third pumps is increased or reduced within a preset control range by a specific amount which is less than a preset limiting value, so that the difference between the weight reduction per unit of time of the sum of the weights of the first container and the third container, and the weight increase per unit of time of the second container, corresponds to a preset value.

17. The device according to claim 16, wherein the control unit is configured such that the preset limiting value is a preset percentage of the preset setpoint delivery rate of the respective first, second, or third pump.

18. The device according to claim 16, wherein the control unit is configured such that the deviation of the adopted delivery quantity of the respective first, second, or third pump at the preset number of revolutions or pump strokes from the measured delivery quantity of the first, second, or third pump at the preset number of revolutions or pump strokes is compared with a preset limiting value, wherein an error signal is generated when the deviation is greater than the limiting value.

19. A blood treatment apparatus comprising:
a first pump for conveying a first fluid from a first container at a first delivery rate into the second chamber of the exchange unit;
a second pump for conveying a second fluid from the second chamber of the exchange unit at a second delivery rate into a second container;
a third pump for conveying a third fluid at a third delivery rate from a third container into the extracorporeal blood circuit;
a first weighing device for determining the sum of the weights of the first container and the third container;
a second weighing device for determining the weight of the second container; and
a control unit for controlling the delivery rates of the pumps, wherein said control unit is configured to balance the fluids as a function of the sum of the weights of the first container and the third container or the weight of the first container, and the weight of the second container; wherein
a weight reduction or a weight increase of at least one of the first, second, or third containers is measured in the time interval in which the first, second or third pump assigned to the respective first, second, or third container performs a preset number of revolutions or pump strokes;
the delivery quantity of the respective first, second, or third pump at the preset number of revolutions or pump strokes is ascertained from the measured weight reduction or weight increase in the time interval;
the setpoint delivery quantity of the first, second, and third pumps at the preset number of revolutions or pump strokes adopted in the drive circuit of the respective first, second, or third pump is compared with the measured delivery quantity of the first, second, or third pump at the preset number of revolutions or pump strokes; and
the drive circuit of the first, second, and third pumps is based on the deviation of the adopted setpoint delivery quantity of the respective first, second, or third pump at the preset number of revolutions or pump strokes from the measured delivery quantity of the first, second, or third pump at the preset number of revolutions or pump strokes.

* * * * *